United States Patent
Yamato et al.

(10) Patent No.: US 6,555,708 B1
(45) Date of Patent: Apr. 29, 2003

(54) N-$^\epsilon$-LONG CHAIN ACYLLSINE CRYSTALS, PROCESS FOR PRODUCING THE SAME AND COSMETICS CONTAINING THE SAME

(75) Inventors: Naoya Yamato, Kanagawa (JP); Yasunori Atarashi, Mie (JP); Keigo Sano, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/048,994

(22) PCT Filed: Aug. 18, 2000

(86) PCT No.: PCT/JP00/05556

§ 371 (c)(1),
(2), (4) Date: Feb. 19, 2002

(87) PCT Pub. No.: WO01/14317

PCT Pub. Date: Jan. 3, 2001

(30) Foreign Application Priority Data

Aug. 19, 1999 (JP) ............................................. 11-232535
Aug. 19, 1999 (JP) ............................................. 11-232537

(51) Int. Cl.$^7$ ..................... C07C 229/00; C07C 205/00; A46B 11/00

(52) U.S. Cl. ........................ 562/575; 523/200; 560/125; 401/126

(58) Field of Search ........................ 562/575; 523/200; 560/125; 401/126

(56) References Cited

FOREIGN PATENT DOCUMENTS

| JP | 1-242563 | * | 9/1989 |
| JP | 8-337519 | * | 12/1996 |
| JP | 9-323914 | | 12/1997 |
| JP | 9-323914 A | * | 12/1997 |

* cited by examiner

Primary Examiner—Alan L. Rotman
Assistant Examiner—Hector M Reyes
(74) Attorney, Agent, or Firm—Oblon, Spivak, McClelland, Maier & Neustadt, P.C.

(57) ABSTRACT

There are provided cosmetics which have not only a reduced effect on the "gleam" caused by irregular light reflection but also a reduced effect on "stickiness" based on an oil raw material, giving a good feeling during use such as spreadability, etc., and being excellent in the sustaining of the makeup effect.

There are used N$^\epsilon$-long chain acyllysine crystals whose average diameter or mode diameter lies in the range of 3~15 $\mu$m without being subjected to the mechanical pulverization.

16 Claims, No Drawings

# N-ε-LONG CHAIN ACYLLSINE CRYSTALS, PROCESS FOR PRODUCING THE SAME AND COSMETICS CONTAINING THE SAME

TECHNICAL FIELD

The present invention relates to $N^\epsilon$-long chain acyllysine crystals. When the $N^\epsilon$-long chain acyllysine crystals were used in cosmetics, there is provided cosmetics which have a good feeling during use such as spreadability, etc., no gleam caused by irregular light reflection, and which reduce the "stickiness" based on the oily raw materials incorporated therein and which are excellent in sustaining the makeup effect.

BACKGROUND ART $N^\epsilon$-Long chain acyllysine has a good lubricity owing to its peculiar plate crystal structure so that it is being used in cosmetics for the purpose of adjusting the feeling, etc. during use. The $N^\epsilon$-long chain acyllysine may be prepared, for example by a process which comprises heating a higher fatty acid salt of lysine at 100~250° C. to cause dehydration (Japanese Patent Application Laid-Open No. 1513/1974). Also, it is known to be prepared by a process which comprises adding crude crystals of $N^\epsilon$-long chain acyllysine to an aqueous medium below pH 2 or above pH 11, dissolving $N^\epsilon$-long chain acyllysine in the aqueous medium by heating the mixture to 40~60° C. while stirring, and thereafter neutralizing the resultant solution to pH 6.5 by adding slowly dropwise a basic medium or an acidic medium while being kept to this temperature thereby $N^\epsilon$-long chain acyllysine is crystallized out.(Japanese Patent Application Laid-Open No. 242563/1989). However, an average particle diameter or a mode diameter of the $N^\epsilon$-long chain acyllysine crystals obtained by these known processes is as large as 15 µm or more so that when they were incorporated into cosmetics there occurs an irregular light reflection due to their plate structure to cause the so-called "gleam". And, in the case of cosmetics where this "gleam" is not preferable, there was a problem that the amount added of the $N^\epsilon$-long chain acyllysine is restricted to some extent.

In this connection, oily raw materials such as an oil and fat, a wax, a hydrocarbon, a fatty acid, a higher alcohol, esters and the like are being used in cosmetics for enhancing emollient effect including controlling transpiration of water from the skin. However, when such oily raw materials were incorporated in a large amount for enhancing emollient effect, the "stickiness" is increased so that the feeling during use is not preferable.

In order to reducing the "stickiness" of the oily raw materials, $N^\epsilon$-long chain acyllysine crystals are known to be incorporated in cosmetics (Japanese Patent Application Laid-Open No. 74312/ 1991).

Since the average particle diameter or the mode diameter of the $N^\epsilon$-long chain acyllysine crystals is as large as 15 µm or more as stated above, their reducing effect on the "stickiness" is small and for this reason their use was not necessarily satisfactory.

On the other hand, as a means of making the particle size of the $N^\epsilon$-long chain acyllysine small, a dry or wet pulverization process is known to be applied to it (Japanese Patent Application Laid-Open No. 323914/1997). Although the pulverized $N^\epsilon$-long chain acyllysine powder which may be obtained by these pulverization processes has not only a little "gleam" caused by the plate structure and but also effect to reduce the "stickiness" based on the oily raw materials, the crystal form is broken owing to the mechanical pulverization to cause the problems that the cosmetics containing it have a bad spreadability and unpleasant feeling when applied to the skin or the hair and that many steps are necessary for its preparation.

Also, as another means to make the particle size small, it is reported that a basic solution of $N^\epsilon$-long chain acyllysine is added dropwise to an acidic solution such as hydrochloric acid thereby obtaining fine crystals of 0.01~3 µm in the terms of the projected diameter when observed under an electron microscope (Japanese Patent Application Laid-Open No. 337519/ 1996). However, when the crystals obtained by this process were measured with a particle size distribution meter, their average particle diameter or their mode diameter lies in the vicinity of 18 µm which does not coincide with the value of the projected diameter observed under the electron microscope, thus they have still large particle size. And therefore, the "gleam" caused by the irregular light reflection due to their plate structure was increased and further the "stickiness" due to the oily raw materials could not be reduced sufficiently and the feeling during use was not satisfactory.

DISCLOSURE OF THE INVENTION

An object of the invention is to provide cosmetics which do not cause any irregular light reflection, i.e. the "gleam" even when applied to the skin and the hair, giving a good feeling during use such as spreadability, etc., and which is excellent in the sustaining of the makeup effect.

Another object of the invention is to provide cosmetics containing an oily raw material, said cosmetics having a high emollient effect and no "stickiness" and being excellent in lubricity during use.

As a result of having ardently studied considering such actual situation, the present inventors have found that by using $N^\epsilon$-long chain acyllysine crystals whose average particle diameter or mode diameter is set to the range of 3~15 µm without being mechanically pulverized there can be provided cosmetics which do not have gleam and stickiness when applied to the skin and the hair, giving a good feeling during use such as spreadability, etc., and being excellent in sustaining the makeup effect. And the present invention has been completed based on the above finding.

That is, the present invention is characterized by being non-pulverized $N^\epsilon$-long chain acyllysine crystals whose average particle diameter and/or mode diameter is 3~15 µm.

Also, the present invention is characterized by being $N^\epsilon$-long chain acyllysine crystals obtained by dissolving $N^\epsilon$-long chain acyllysine in an acidic solvent or a basic solvent consisting of one or more selected from lower alcohols and/or water and thereafter neutralizing the resultant solution by adding dropwise a basic solution or an acidic solution at a temperature below 35° C. to crystallize out $N^\epsilon$-long chain acyllysine.

Also, the present invention relates to powders treated wherein powders for cosmetic use have been subjected to dry surface treatment with one or more selected from said crystals.

Further, the present invention is cosmetics which are characterized by containing said crystals or said powders treated.

Furthermore, the present invention is cosmetics which are characterized by containing an oily raw material in combination with said crystals.

Also, the present invention relates to a process for preparing $N^\epsilon$-long chain acyllysine crystals which is characterized by dissolving $N^\epsilon$-long chain acyllysine in an acidic solvent or a basic solvent consisting of one or more selected from lower alcohols and/or water and thereafter neutralizing the resultant solution by adding dropwise a basic solution or an acidic solution at a temperature below 35° C. to crystallize out $N^\epsilon$-long chain acyllysine.

Firstly, $N^\epsilon$-long chain acyllysine crystals of the present invention and a process for preparing the same are illustrated.

The raw material $N^\epsilon$-long chain acyllysine which may be employed in a process for preparing crystals of the present invention may be synthesized by the known process described in Japanese Patent Application Laid-Open No. 1513/1974. Also, a commercially available product (for example, "Amihope", a trade name, a product of Ajinomoto Co., Inc.) may be employed.

The long chain acyl groups in the $N^\epsilon$-long chain acyllysine are those of saturated or unsaturated fatty acids having 8~22 carbon atoms. If they are exemplified, oleyl, lauroyl, myristyl, stearyl, palmityl, octyldodecyl, behenyl, acyl of coconut oil fatty acid, acyl of palm kernel oil fatty acid, acyl of tallow oil fatty acid and so on are taken, but lauroyl group is preferred from the standpoint of view of being widely available.

Also, $N^\epsilon$-long chain acyllysine for use in the present invention may be represented by the following general formula (1)

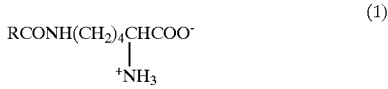

(wherein R represents a straight or branched chain alkyl or alkenyl group having 7~21 carbon atoms)

As examples of a lower alcohol which may be employed for the crystallization, aliphatic alcohols having 1~4 carbon atoms such as methanol, ethanol, propanol, butanol, isopropanol and the like are taken. However, methanol, ethanol, isopropanol are preferred. These lower alcohols may be used singly or in admixture with two or more of kinds.

The ratio of lower alcohol to water is not limited particularly and it may be in the range of lower alcohol/water=0/100~100/0, preferably 55/45~70/30 in terms of weight ratio. That is, in the case that the weight ratio of the both is smaller than 55/45 or otherwise in the case that it is larger than 70/30, the solubility of the $N^\epsilon$-long chain acyllysine is decreased so that a large amount of the solvent is needed for dissolving it and the efficiency is lowered.

Next, to the above solvent is added an acid or a base to make an acidic or basic solvent which dissolves the $N^\epsilon$-long chain acyllysine.

As an acid to be used, it may be either an organic acid or an inorganic acid. If it is exemplified, sulfuric acid, hydrochloric acid, nitric acid, phosphoric acid, citric acid, lactic acid, glutamic acid, pyrrolidonecarboxylic acid and the like are taken, but sulfuric acid and hydrochloric acid are preferred.

As a base to be used, it may be either an organic base or an inorganic base. For example, sodium hydroxide, potassium hydroxide, calcium hydroxide, barium hydroxide, sodium carbonate, ammonia, triethylamine, triethanolamine, monoethanolamine, pyridine and the like are taken, but sodium hydroxide and potassium hydroxide are preferred.

The amount of the acid or the base to be added in this case is not limited particularly and it may be any one if it is sufficient to dissolve $N^\epsilon$-long chain acyllysine.

Next, the acidic solvent or the basic solvent in which N-long chain acyllysine has been dissolved is kept to a temperature below 35° C. and neutralized by adding dropwise a basic solution or an acidic solution to crystallize out N-long chain acyllysine.

The temperature at which the crystallization is conducted is not limited particularly so long as it is below 35° C. However, the temperature below 28° C. is particularly preferable from the standpoint of view that the crystals having a small average particle diameter and/or mode diameter may be obtained. Also, the lower limitation of the crystallization temperature may be below the coagulation point of the solvent used.

When the crystallization temperature exceeds 35° C., the obtained $N^\epsilon$-long chain acyllysine crystals have such a large average particle diameter and mode diameter as 15 μm or more and become thick and plate crystal so that when they were incorporated into cosmetics, not only the gleam is recognized due to their plate structure but also the "stickiness" based on the oily raw material can not be reduced sufficiently because of their large size diameter, thus being not preferable.

The basic or acidic solution for use in the crystallization may be prepared with the acid or the base as stated above.

The process to isolate and dry the formed crystals may be conducted according to the conventional manner.

The crystals obtained according to the present invention have an average diameter and a mode diameter of 3~15 μm when measured with a particle size distribution meter of LS230 type manufactured by Coulter Inc.

The measurement of the average diameter and the mode diameter is conducted by using isopropanol as a dispersing solvent, adjusting the concentration of the compound to be tested in said dispersing solvent so as to become about 16% and controlling the circulation speed so as to be 10 L/min.

The average diameter and the mode diameter defined herein are ones determined using a volume cumulative value. Also, the mode diameter means the particle size which becomes the maximum frequency.

The followings illustrate the powders treated which is characterized by having subjected powders for cosmetic use to dry surface treatment with one or more selected from said crystals.

The powders for cosmetic use which may be used in the present invention are not particularly limited if they are ones (pigments, coloring materials, resins) used in cosmetics. Examples of such powders include resin powders such as nylon beads, silicone beads and the like; nylon powder, metallic fatty acid soap, yellow iron oxide, red iron oxide, black iron oxide, chromium oxide, cobalt oxide, carbon black, Ultramarine, iron blue, zinc oxide, titanium oxide, zirconium oxide, silicon dioxide, aluminum oxide, cerium oxide, mica titanium, boron nitride, barium sulfate, calcium carbonate, magnesium carbonate, aluminum silicate, magnesium silicate, silicon carbide, pigment, lake, sericite, mica, talc, kaolin, plate barium sulfate, butterfly barium sulfate, fine particle titanium oxide, fine particle zinc oxide, fine particle iron oxide and the like. Furthermore, they may be ones wherein there has been applied a surface-treatment such as silicon-treatment, fluorine compound-treatment, silane coupling agent-treatment, silane treated organic titanate-treatment, fatty acid-treatment, metallic soap-treatment, oil agent-treatment, amino acid-treatment or the like. The process for surface-treatment may be conducted by a dry treatment usually used.

Next, cosmetics which are characterized by containing said N-long chain acyllysine crystals or said powders treated are illustrated.

Although the amount of said crystals or said powders treated to be incorporated into cosmetics may be greatly varied depending on the form of cosmetics, it is 0.1~99% by weight in makeup and basic cosmetics while it is 0.1~30% by weight in hair and cleaning cosmetics.

Next, an oily raw material for use in the present invention is not limited particularly and there may be used oils which have been widely used as the raw material for cosmetics.

Examples of an oil include higher alcohols such as cetyl alcohol, isostearyl alcohol, lauryl alcohol, hexadexyl alcohol, octyl dodecanol and the like; fatty acids such as isostearic acid. undecylic acid, oleic acid and the like; polydric alcohols such as glycerin, sorbitol, ethylene glycol, propylene glycol, polyethlene glycol and the like; esters such as myristyl myristate, hexyl laurate, decyl oleate, isopropyl myristate, hexyldecyl dimethyloctanoate, glycerol monostearate, diethyl phthalate, ethylene glycol monostearate, octyl hydroxystearate and the like; hydrocarbons such as liquid paraffin, vaseline, squalane and the like; waxes such as lanolin, hydrogenated lanolin, carnauba wax and the like; fat and oils such as mink oil, cacao oil, coconut oil, palm kernel oil, camellia oil, sesame oil, castor oil, olive oil and the like; ethylene-α-olefin co-oligomer and the like.

Also, examples of another form of oils include silicone compounds such as dimethyl polysiloxane, methyl hydrogen polysiloxane, methyl phenyl polysiloxane, polyether-modified organopolysiloxane, fluoroalkyl polyoxyalkylene co-modified organopolysiloxane, alkyl-modified organopolysiloxane, terminal-modified organopolysiloxane, fluoro-modified organopolysiloxane, aminodimethicone, amino-modified organopolysiloxane, silicone gel, acryl silicone, trimethylsiloxy silicic acid, silicone RTV rubber and the like; fluorine compounds such as perfluorocarbon, fluoroalcohol and the like.

In addition to the above components, there may be incorporated into the cosmetics of the present invention at the same time components usually used in cosmetics inclusive a fluorine compound, a resin, a surfactant, a thickener, a high molecular compound, an antiseptic, a perfume, an ultraviolet absorber (includes an organic and an inorganic ones, and may be one susceptible to either UV-A or UV-B), a humectant, a hystologically active substance, salts, a solvent, an antioxidant, an antibacterial agent, an anhidrotics, a chelating agent, a neutralizer, a pH adjusting agent and the like.

As a surfactant, for example an anionic surfactant, a cationic surfactant, a nonionic surfactant and betaine type surfactant may be used.

Examples of an organic ultraviolet absorber include 2-ethylhexyl p-methoxy cinnamate, 2-ethylhexyl p-dimethyl-aminobenzoate, 2-hydroxy-4-methoxybenzophenone-5- sulfuric acid, 2,2'-dihydroxy-4-methoxybenzophenone, diethanolamine salt of p-methoxyhydrocinnamic acid, p-aminobenzoic acid (hereinafter, referred to as PABA), ethyl dihydroxy propyl PABA, gryceryl PABA, homomethyl salicylate, methyl-o-aminobenzoate, 2 - ethylhexyl- 2 - cyano- 3,3 - diphenylacrylate, octyl dim ethyl PABA, octyl methoxycinnamate, 2-phenyl-benzimidazole-5-sulfuric acid, triethanolamine salt of salicylic acid, 3-(4-methylbenzylidene) camphor, 2,4-dihydroxybenzophenone, 2,2', 4,4'-tetrahydroxy-benzophenone, 2,2'-dihydroxy-4,4'-dimethoxybenzophenone, 2-hydroxy-4-N-octoxybenzophenone, 4-isopropyl dibenzoylmethane, butyl methoxy dibenzoylmethane, 2-ethylhexyl 4-(3, 4-dimethoxyphenymethylene) -2, 5-dioxo- 1-imidazolidine propionate and the like.

Examples of the solvent include cyclic silicone, ethanol, soft liquid isoparaffin, lower alcohol, ethers, LPG, fluorocarbon, N-methylpyrrolidone, fluoroalcohol, volatile straight chain silicone and the like.

The cosmetics of the present invention may be any form inclusive powders, liquid, cream, paste, cake and solid. Specifically, makeup cosmetics such as a foundation, a face powder, a cheek rouge, an eye shadow and the like; body cosmetics such as a body powder, a baby powder and the like;

basic cosmetics such as a lotion, a milky lotion, a facial liquid essence, a skin cream, a sun care product and the like; cleaning agents such as a cleansing powder, a hair shampoo, a body shampoo, a hand soap, a solid soap and the like; hair cosmetics such as a rinse, a treatment, a styling agent, an anhidrotics, a bathing agent, a hair dye and the like.

The cosmetics of the present invention may be prepared according to the conventional process.

Best Modes For Carrying Out the Invention

The following examples illustrate the present invention in more detail, but the present invention is not limited to these examples.

PREPARATION EXAMPLE 1

5.7 Grams of sodium hydroxide was dissolved in a mixed solution of 97.4 g of methanol and 62.7 g of water at room temperature and thereafter the solution was heated to about 50° C., and 36.4 g of $N^\epsilon$-lauroyllysine was added thereto and dissolved at this temperature. And then, the resultant solution was cooled to 25° C. and 38.0 g of 17.5% hydrochloric acid was added dropwise thereto at this temperature over about 4 hours to adjust the pH to 7.0 thereby the precipitated crystals were filtered out and dried under reduced pressure to obtain 35.6 g (yield: 97.8%) of white crystals. The crystals were measured for their average diameter and for their mode diameter using a particle size distribution meter LS230 type manufactured by Coulter Inc. wherein isopropanol was used as a dispersing solvent, and an absorbance and a circulation speed were set to about 16% and to 10 L/min., respectively. As a result, the average diameter and the mode diameter determined using volume cumulative value were 6 $\mu$m and 7 $\mu$m, respectively.

PREPARATION EXAMPLE 2

5.7 Grams of sodium hydroxide was dissolved in a mixed solution of 97.4 g of methanol and 62.7 g of water at room temperature and thereafter the solution was heated to about 50° C., and 36.4 g of $N^\epsilon$-lauroyllysine was added thereto and dissolved at this temperature. And then, the resultant solution was cooled to 10° C. and 38.0 g of 17.5% hydrochloric acid was added dropwise thereto at this temperature over about 4 hours to adjust the pH to 7.0 thereby the precipitated crystals were filtered out and dried under reduced pressure to obtain 35.0 g (yield: 96.1%) of white crystals. The crystals were measured for their average diameter and for their mode diameter using a particle size distribution meter LS230 type manufactured by Coulter Inc. wherein isopropanol was used as a dispersing solvent, and an absorbance and a circulation speed were set to about 16% and to 10 L/min., respectively. As a result, the average diameter and the mode diameter determined using volume cumulative value were 7 $\mu$m and 7 $\mu$m, respectively.

PREPARATION EXAMPLE 3

5.7 Grams of sodium hydroxide was dissolved in a mixed solution of 97.4 g of methanol and 62.7 g of water at room temperature and thereafter the solution was heated to about 50° C., and 36.4 g of N$^\epsilon$-lauroyllysine was added thereto and dissolved at this temperature. And then, the resultant solution was cooled to 20° C. and 38.0 g of 17.5% hydrochloric acid was added dropwise thereto at this temperature over about 4 hours to adjust the pH to 7.0 thereby the precipitated crystals were filtered out and dried under reduced pressure to obtain 35.1 g (yield: 96.4%) of white crystals. The crystals were measured for their average diameter and for their mode diameter using a particle size distribution meter LS230 type manufactured by Coulter Inc. wherein isopropanol was used as a dispersing solvent, and an absorbance and a circulation speed were set to about 16% and to 10 L/min., respectively. As a result, the average diameter and the mode diameter determined using volume cumulative value were 6 μm and 10 μm, respectively.

PREPARATION EXAMPLE 4

5.7 Grams of sodium hydroxide was dissolved in a mixed solution of 97.4 g of methanol and 62.7 g of water at room temperature and thereafter the solution was heated to about 50° C., and 36.4 g of N$^\epsilon$-lauroyllysine was added thereto and dissolved at this temperature. And then, the resultant solution was cooled to 30° C. 38.0 g of 17.5% hydrochloric acid was added dropwise thereto at this temperature over a period of about 4 hours to adjust the pH to 7.0. The precipitated crystals were filtered out and dried under reduced pressure to obtain 36.1 g (yield: 99.2%) of white crystals. The crystals were measured for their average diameter and for their mode diameter using a particle size distribution meter LS230 type manufactured by Coulter Inc. wherein isopropanol was used as a dispersing solvent, and an absorbance and a circulation speed were set to about 16% and to 10 L/min., respectively. As a result, the average diameter and the mode diameter determined using volume cumulative value were 14 μm and 15 μm, respectively.

COMPARATIVE PREPARATION EXAMPLE 1

(Neutralizing crystallization at 40° C.)

10 Grams of N$^\epsilon$-lauroyllysine were added to a mixed solution of methanol and 10% aqueous sodium hydroxide solution (2:1) and dissolved at 40° C. under stirring. While the temperature was constantly kept to 40° C., the solution was neutralized to pH 6.5 by adding 10% aqueous hydrochloric acid solution dropwise. The precipitated crystals were filtered out and dried under reduced pressure to obtain 9.6 g of white and plate crystals. The crystals were measured for their average diameter and for their mode diameter using a particle size distribution meter LS230 type manufactured by Coulter Inc. wherein isopropanol was used as a dispersing solvent, and an absorbance and a circulation speed were set to about 16% and to 10 L/min., respectively. As a result, the average diameter and the mode diameter determined using volume cumulative value were 21 μm and 20 μm, respectively.

COMPARATIVE PREPARATION EXAMPLE 2

(Process described in Preparation Example 1 of Japanese Patent Application Laid-Open No. 337519/1996)

30 Grams of N$^\epsilon$-lauroyllysine were dissolved in 150 ml of 10% aqueous sodium hydroxide solution, and the solution was added dropwise to 200 ml of 2 mol/l aqueous hydrochloric acid solution while stirring. After the total amount of the solution was added dropwise, the pH of the resultant solution was adjusted to 5. The precipitated crystals were filtered out and dried to obtain 29.6 g of white crystals. The crystals were measured for their average diameter and for their mode diameter using a particle size distribution meter LS230 type manufactured by Coulter Inc., wherein isopropanol was used as a dispersing solvent, and an absorbance and a circulation speed were set to about 16% and to 10 L/min., respectively. As a result, the average diameter and the mode diameter determined using volume cumulative value were 18 μm and 20 μm, respectively.

COMPARATIVE PREPARATION EXAMPLE 3

(Wet pulverization process)

250 Grams of ethanol was added to 25 g of N$^\epsilon$-lauroyllysine and the mixture was stirred and rotated with a ball mill for 3 hours. As the powder medium there was used one having a particle size of 5 mm which had been made from agate. A slurry after pulverization was heated under reduced pressure to distill off the solvent and thereafter the residue was coarsely ground with a mixer to obtain the intended and finely ground N-lauroyllysine powder. The powder was measured for its average diameter and for its mode diameter using a particle size distribution meter LS230 type manufactured by Coulter Inc. wherein isopropanol was used as a dispersing solvent, and an absorbance and a circulation speed were set to about 16% and to 10 L/min., respectively. As a result, the average diameter and the mode diameter determined using volume cumulative value were 3 μm and 6 μm, respectively.

COMPARATIVE PREPARATION EXAMPLE 4

(Dry pulverization process)

N$^\epsilon$-Lauroyllysine was pulverized by dry process using a supersonic JET grinder manufactured by Nippon Pneumatic Mfg. Co., Ltd. The pulverized product was measured for its average diameter and for its mode diameter using a particle size distribution meter LS230 type manufactured by Coulter Inc. wherein isopropanol was used as a dispersing solvent, and an absorbance and a circulation speed were set to about 16% and to 10 L/min., respectively. As a result, the average diameter and the mode diameter determined using volume cumulative value were 10 μm and 9 μm, respectively.

EXPERIMENTAL EXAMPLE 1

(Test method for evaluating gleam)

A variety of N$^\epsilon$-Lauroyllysine powders were spread to each front arms of five panelists consisting of men and women, and the extent of the gleam was visually evaluated. The evaluation was made by 3-grades of 0 point (appreciable gleam is recognized) ~2 points (no gleam) and the average value was calculated. The average value of above 0 point and less than 0.7 point was assigned to X, that of above 0.7 point and less than 1.4 points was assigned to Δ and that of above 1.4 points and less than 2.0 points was assigned to ○. The results are shown in table 1.

TABLE 1

| | Crystallization temperature or Preparation process | Average particle size (μm) | Gleam | Spread-ability |
|---|---|---|---|---|
| Preparation Example 1 | Crystallization temperature: 25° C. | 6 | ○ | ○ |
| Preparation Example 2 | Crystallization temperature: 10° C. | 7 | ○ | ○ |
| Preparation Example 3 | Crystallization temperature: 20° C. | 6 | ○ | ○ |
| Preparation Example 4 | Crystallization temperature: 30° C. | 14 | ○ | ○ |
| Comparative Preparation Example 1 | Crystallization temperature: 40° C. | 21 | x | ○ |
| Comparative Preparation Example 2 | Process described in Japanese Patent Application Laid-Open No. 337519/1996 | 18 | x | ○ |
| Comparative Preparation Example 3 | Wet pulverization process | 3 | ○ | x |
| Comparative Preparation Example 4 | Dry pulverization process | 10 | ○ | x |

It can be seen from table 1 that the products of the present invention have less gleam in comparison with comparative products.

EXPERIMENTAL EXAMPLE 2

(Test method evaluating spread ability)

Since the extent of spreadability is dependant on the frictional force between the skin and the powders spread thereto, a variety of powders were measured for their dynamic friction coefficience with a friction tester (a product of Kato Tech Co., Ltd.) according to the following method thereby the evaluation test of spreadability was conducted.

A double face adhesive tape (a product of Lion Co., Ltd.) was applied to a slide glass in a longitudinal direction and each of various $N^\epsilon$-lauroyllysine powders was uniformly spread to the surface of the tape. After the superfluous powders were fallen from the surface of the tape by tapping the back side of the slide glass with a finger, a probe equipped with a silicone rubber (weight:50 g) was slid to measure dynamic friction coefficience (a friction tester, a product of Kato Tech Co., Ltd.). Evaluation was made by assigning respectively a dynamic friction coefficience below 0.25 to ○, that ranging 0.25~0.35 to and that above 0.35 to X. The results are shown in table 1.

As can be seen from table 1, the products of the present invention have a good feeling during use such as spreadability, etc.

FORMULATION EXAMPLE 1

5 Grams of $N^\epsilon$-lauroyllysine crystals obtained in Preparation Example 1 and 95 g of talc (a product of Nippon Talc Co., Ltd., a trade name, "Micro Ace P-30") each weighed and were mixed together under stirring to obtain a face powder.

EXPERIMENTAL EXAMPLE 3

(Test method for evaluating the sustaining of the makeup effect)

Since the extent of sustaining the makeup effect is dependant on the difficulty in the makeup-comes-off of the makeup by waterdrop and sweat, the water repellency of powders was evaluated by measuring the contact angle between the powder and water thereby the evaluation test was conducted with respect to the sustaining of the makeup effect.

0.15 Gram of the face powder obtained in the above Formulation Example 1 was pressed for 1 min. under a pressure of 300 kg/cm 2 with IR tablet compressing machine. On the pressed face powder was added dropwise 3 ml of water and the contact angle after 60 second was measured. Evaluation was made by assigning respectively a contact angle after 60 second above 90 degree to ○, that ranging from 70 to 90 degree to A and that below 70 degree to X.

As a comparative example, 5 g of N-lauroyllysine crystals obtained in Comparative Preparation Example 1 and 95 g of talk (a product of Nippon Talk Co., Ltd., a trade name, "Micro Ace P-30") were mixed together under stirring. The contact angle was similarly measured with respect to the obtained face powder. The results are shown in table 2.

TABLE 2

| | (% by weight) | |
|---|---|---|
| | Formulation Example | Comparative Formulation Example |
| Crystals of Preparation Example 1 | 5 | — |
| Crystals of Comparative Preparation Example 1 | — | 5 |
| Talc | 95 | 95 |
| The sustaining of the makeup effect | ○ | Δ |

As can be seen from table 2, the face powder obtained in Comparative Formulation Example has a low water repellency so that when it was applied to the skin and the hair, the makeup-comes-off of the makeup by waterdrop and sweat occurs easily while the face powder of the present invention has a high water repellency so that the makeup-comes-off of the makeup by waterdrop and sweat occurs with difficulty, thus it is excellent in the sustaining of the makeup effect.

FORMULATION EXAMPLE 2 AND EXPERIMENTAL EXAMPLE 4

Powder foundations were prepared having compositions shown in table 3 and each of the powder foundations was applied to the front arms of 8 panelists consisting of men and women, and its "stickiness", "gleam" and "lubricity" during use were evaluated sensually and visually. The evaluation was made in 5-grades of 1 point (bad="stickiness" or "gleam" is appreciable or "rubricity" is bad) to 5 points (good=no "stickiness" or no "gleam" or "lubricity" is good), and the average value was lo calculated. The average value above 4.1 was assigned to ⊚, that ranging 3.1 4.0 was assigned to ○, that ranging 2.1~3.0 was assigned to Δ and that below 2 was assigned to X. The results are shown in table 3.

TABLE 3

% by weight

| | Formulation Example 2 | Comparative Formulation Example | | | |
|---|---|---|---|---|---|
| Talc | 30.0 | 30.0 | 30.0 | 30.0 | 30.0 |
| Sericite | 30.0 | 30.0 | 30.0 | 30.0 | 30.0 |
| Mica | 10.0 | 10.0 | 10.0 | 10.0 | 10.0 |
| Magnesium stearate | 2.0 | 2.0 | 2.0 | 2.0 | 2.0 |
| Titanium oxide | 8.0 | 8.0 | 8.0 | 8.0 | 8.0 |
| Powder of Preparation Example 1 | 10.0 | | | | |
| Powder of Comparative Preparation Example 1 | | 10.0 | | | |
| Powder of Comparative Preparation Example 2 | | | 10.0 | | |
| Powder of Comparative Preparation Example 3 | | | | 10.0 | |
| Powder of Comparative Preparation Example 4 | | | | | 10.0 |
| Silicone oil | 6.0 | 6.0 | 6.0 | 6.0 | 6.0 |
| Octyl dodecanol | 4.0 | 4.0 | 4.0 | 4.0 | 4.0 |
| Stickiness | ⊚ | ○ | ○ | ⊚ | ⊚ |
| Gleam | ⊚ | Δ | Δ | ⊚ | ⊚ |
| Lubricity | ⊚ | ⊚ | ⊚ | Δ | Δ |

As can be seen from table 3, the product of the present invention has no defect in such feeling during use as "stickiness" and "gleam", and is excellent in "lubricity" in comparison with the comparison products.

FORMULATION EXAMPLE 3 AND EXPERIMENTAL EXAMPLE 5

Milky lotions were prepared having compositions shown in table 4 and each of the powder foundations was applied to the front arms of 8 panelists consisting of men and women, and its "stickiness", "gleam" and "lubricity" during use were evaluated sensually and visually. The evaluation was made in 5-grades of 1 point (bad="stickiness" or "gleam" is appreciable or "lubricity"is bad) to 5 points (good=no "stickiness" or no "gleam" or "lubricity " is good), and the average value was calculated. The average value above 4.1 was assigned to ⊚, that ranging 3.1 4.0 was assigned to ○, that ranging 2.1~3.0 was assigned to Δ and that below 2 was assigned to X. The results are shown in table 4.

The preparation of the milky lotion was conducted by dissolving individually the oil phase components and the aqueous phase components under heating, adding slowly the aqueous phase to the oil phase under stirring and emulsifying the combined phases with a homomixer.

TABLE 4

% by weight

| | | Formulation Example 3 | Comparative Formulation Example | | | |
|---|---|---|---|---|---|---|
| Oil phase component | Liquid paraffin | 5.0 | 5.0 | 5.0 | 5.0 | 5.0 |
| | Dioctyldodecyl lauroylglutamate | 2.0 | 2.0 | 2.0 | 2.0 | 2.0 |
| | Propylene glycol monostearate | 0.5 | 0.5 | 0.5 | 0.5 | 0.5 |
| | POE (5) hardened castor oil | 1.5 | 1.5 | 1.5 | 1.5 | 1.5 |
| | POE (5) glyceryl monostearate | 2.5 | 2.5 | 2.5 | 2.5 | 2.5 |
| | Butylparaben | 0.1 | 0.1 | 0.1 | 0.1 | 0.1 |
| | Powder of Preparation Example 1 | 3.0 | | | | |
| | Powder of Comparative Preparation Example 1 | | 3.0 | | | |
| | Powder of Comparative Preparation Example 2 | | | 3.0 | | |
| | Powder of Comparative Preparation Example 3 | | | | 3.0 | |
| | Powder of Comparative Preparation Example 4 | | | | | 3.0 |
| Aqueous phase component | Sodium N-stearyl L-glutamate | 0.3 | 0.3 | 0.3 | 0.3 | 0.3 |
| | Carboxy vinyl polymer | 0.2 | 0.2 | 0.2 | 0.2 | 0.2 |
| | Sodium hydroxide | 0.08 | 0.08 | 0.08 | 0.08 | 0.08 |
| | 1,3-Butylene glycol | 5.0 | 5.0 | 5.0 | 5.0 | 5.0 |
| | Methylparaben | 0.1 | 0.1 | 0.1 | 0.1 | 0.1 |
| | Purified water | Remainder | Remainder | Remainder | Remainder | Remainder |
| | Stickiness | ⊚ | ○ | ○ | ⊚ | ⊚ |
| | Gleam | ⊚ | Δ | Δ | ⊚ | ⊚ |
| | Lubricity | ⊚ | ⊚ | ⊚ | Δ | Δ |

As can be seen from table 4, the product of the present invention has no defect in such feeling during use as "stickiness" and "gleam" and is excellent in "lubricity" in comparison with the comparison products.

FORMULATION EXAMPLE 4 LIQUID FOUNDATION

A liquid foundation was prepared having a composition shown in table 4 and there was obtained the liquid foundation having no disadvantage in such feeling during use as "stickiness" and "gleam", and having an excellent "lubricity".

TABLE 5

|  | (% by weight) |
| --- | --- |
| Stearic acid | 3.0 |
| Isopropyl stearate | 9.0 |
| Liquid paraffin | 1.5 |
| Cetanol | 1.0 |
| Powder of Preparation Example 1 | 6.0 |
| Triethanolamine | 1.5 |
| Propylene glycol | 5.0 |
| Glycine betaine | 2.0 |
| Bentonite (1% aqueous solution) | 15.0 |
| Purified water | Remainder |

FORMULATION EXAMPLE 5 LIPSTICK

Pigment components shown in table 5 were mixed together with a high speed mill and mixed with oil phase components which had been allowed to be dissolved by heating, and the mixture was kneaded with rolls. And then, the mixture was twice was dissolved by heating. After defoaming, it was molded to prepare a lipstick having no defect in such feeling during use as "stickiness" and "gleam", and having an excellent "lubricity" after use.

TABLE 6

|  | (% by weight) |
| --- | --- |
| Oil phase component | |
| Carnauba wax | 2 |
| Candelilla wax | 6.5 |
| Beeswax | 5.5 |
| Hardened castor oil | 2 |
| Liquid lanolin | 16.8 |
| Microcrystalline wax | 3 |
| Octyldodecanol | 15 |
| Octyldodecyl myristate | 9.5 |
| Castor oil | 23.7 |
| Pigment component | |
| Pearl pigment | 2 |
| Titanium oxide | 1.5 |
| Powder of Preparation Example 1 | 9 |
| Red oxide | 1.3 |
| Red No. 202 pigment | 2.2 |

FORMULATION EXAMPLE 5 HAIR TREATMENT

Oil phase components and aqueous phase components shown in table 7 were separately mixed under heating, and the aqueous phase components were added to the oil phase components. The resultant mixture was emulsified with a homomixer and cooled to 40° C. on standing while stirring. A perfume was added thereto to prepare a hair treatment having no defect in such feeling during use as "stickiness" and "gleam", and having an excellent "lubricity" after use.

TABLE 7

|  | (% by weight) |
| --- | --- |
| Oil phase component | |
| Liquid paraffin | 3.5 |
| Cetanol | 5.0 |

TABLE 7-continued

|  | (% by weight) |
| --- | --- |
| Self-emulsifiable type glycerin monostearate | 6.0 |
| Pyroglutamic acid isostearic acid polyoxyethylene glyceryl | 1.0 |
| Dioctyldodecyl NH auroylglutamate | 2.0 |
| Aqueous phase component | |
| Powder of Preparation Example 1 | 3.0 |
| 1,3-Butylene glycol | 3.0 |
| Glycine betaine | 7.0 |
| Stearyl trimethylammonium chloride | 1.5 |
| Distearyl dimethylammonium chloride | 1.5 |
| Purified water | Remainder |
| Perfume | 0.2 |

Industrial Applicability

According to the present invention, there can be provided cosmetics which cause neither "gleam" nor "stickiness" when applied to the skin and the hair, giving a good feeling during use such as spreadability, etc., and being excellent in the sustaining of the makeup effect in the formulation.

What is claimed is:

1. A non-pulverized $N^\epsilon$-long chain acyllysine crystal having an average particle diameter of from 3 to 15 $\mu$m.

2. The $N^\epsilon$-long chain acyllysine crystal according to claim 1 wherein the $N^\epsilon$-long chain acyllysine is represented by formula (1)

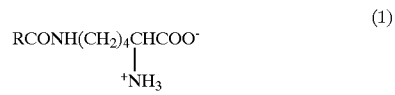

(1)

wherein R represents a straight or branched chain alkyl or alkenyl group having from 7 to 21 carbon atoms.

3. A cosmetic comprising the $N^\epsilon$-long chain acyllysine crystal according to claim 1.

4. The cosmetic according to claim 3 further comprising an oil raw material.

5. A powder made by a process of dry surface treating a powder for cosmetic use with the $N^\epsilon$-long chain acyllysine crystal according to claim 1.

6. A cosmetic comprising the powder according to claim 5.

7. The cosmetic according to claim 6 further comprising an oil raw material.

8. A process for preparing the $N^\epsilon$-long chain acyllysine crystal of claim 1 said process comprising dissolving an $N^\epsilon$-long chain acyllysine in an acidic solvent or a basic solvent comprising at least one member selected from the group consisting of a lower alcohol and water; and adding dropwise a basic solution or an acidic solution at a temperature below 35° C. to crystallize out the $N^\epsilon$-long chain acyllysine.

9. A non-pulverized $N^\epsilon$-long chain acyllysine crystal having a mode diameter of from 3 to 15 $\mu$m.

10. The $N^\epsilon$-long chain acyllysine crystal according to claim 9 wherein the $N^\epsilon$-long chain acyllysine is represented by formula (1).

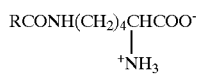

(1)

wherein R represents a straight or branched chain alkyl or alkenyl group having from 7 to 21 carbon atoms.

11. A cosmetic comprising the $N^\epsilon$-long chain acyllysine crystal according to claim 9.

12. The cosmetic according to claim 11 further comprising an oil raw material.

13. A powder made by a process of dry surface treating a powder for cosmetic use with the $N^\epsilon$-long chain acyllysine crystal according to claim 9.

14. A cosmetic comprising the powder according to claim 13.

15. The cosmetic according to claim 14 further comprising an oil raw material.

16. A process for preparing the $N^\epsilon$-long chain acyllysine crystal of claim 9, said process comprising dissolving an $N^\epsilon$-long chain acyllysine in an acidic solvent or a basic solvent comprising at least one member selected from the group consisting of a lower alcohol and water; and adding dropwise a basic solution or an acidic solution at a temperature below 35° C. to crystallize out the $N^\epsilon$-long chain acyllysine.

* * * * *

UNITED STATES PATENT AND TRADEMARK OFFICE
CERTIFICATE OF CORRECTION

PATENT NO.      : 6,555,708 B1                                          Page 1 of 1
DATED           : April 29, 2003
INVENTOR(S)     : Naoya Yamato et al.

It is certified that error appears in the above-identified patent and that said Letters Patent is hereby corrected as shown below:

<u>Title page, Item [54] and Column 1, lines 1 thru 3,</u>
The Title, should read:
-- [54]  N-EPSILON-LONG CHAIN ACYLLYSINE CRYSTALS, PROCESS FOR PRODUCING THE SAME AND COSMETICS CONTAINING THE SAME --
Item [87], the PCT Publication Date, should read:
-- [87]  PCT Pub. No.: WO01/14317
         PCT Pub. Date: Mar. 1, 2001 --

Signed and Sealed this

Second Day of September, 2003

JAMES E. ROGAN
*Director of the United States Patent and Trademark Office*